United States Patent
Kao et al.

(10) Patent No.: US 6,171,284 B1
(45) Date of Patent: Jan. 9, 2001

(54) SYRINGE NEEDLE COVER STRUCTURE

(76) Inventors: Wang-Hsiang Kao; Kuei-Chun Chen, both of P.O. Box No. 6-57, Chung-Ho City, Taipei Hsien 235 (TW)

(*) Notice: Under 35 U.S.C. 154(b), the term of this patent shall be extended for 0 days.

(21) Appl. No.: 09/526,181

(22) Filed: Mar. 15, 2000

(51) Int. Cl.[7] ....................................... A61M 5/32
(52) U.S. Cl. ........................... 604/192; 604/198; 604/263
(58) Field of Search ..................................... 604/192, 198, 604/263, 187, 110

(56) References Cited

U.S. PATENT DOCUMENTS

| | | | |
|---|---|---|---|
| 5,269,765 | * 12/1993 | Kuracina | 604/192 |
| 5,292,314 | * 3/1994 | D'Alessio et al. | 604/263 X |
| 5,295,963 | * 3/1994 | Deeks | 604/198 X |
| 5,364,370 | * 11/1994 | Szerlip et al. | 604/192 |
| 5,478,313 | * 12/1995 | White | 604/192 |
| 5,582,597 | * 12/1996 | Brimhall et al. | 604/192 |

* cited by examiner

Primary Examiner—John D. Yasko

(57) ABSTRACT

An improved structure syringe needle cover comprised of a sleeve, a coil spring, and a mount, wherein the sleeve is installed over the syringe needle and has minute hole disposed through it and, furthermore, a press release section is situated along the two exterior sides of the protective head thereby formed, with a hollow expandable and contractible space having a number of break lines along the two sides extending through its center section. Formed in the lower section is a passage that is aligned with the minute hole of the upper section and has an annular groove disposed around the exterior and, furthermore, there is a conjoinment section at the two sides of the annular groove. The coil spring is installed into the center section of the sleeve and the mount is then attached to the lower section of the said sleeve, with the latch tabs extending from its two sides engaged to the center section of the sleeve and, furthermore, there is a catch section at the lower end of the latch tabs that engages the conjoinment section at the lower section of the sleeve. With the structure of the present invention is installed over a syringe needle, the user only has to pull down the protective head and is not required to remove a syringe needle cover to utilize the syringe. Following utilization, the mount is rotated counter-clockwise to re-cover the syringe needle to achieve safe performance that prevents accidental user needlestick injury and pathogenic transmission due to blood contamination, thereby protecting medical treatment personnel and reducing medical treatment costs.

1 Claim, 7 Drawing Sheets

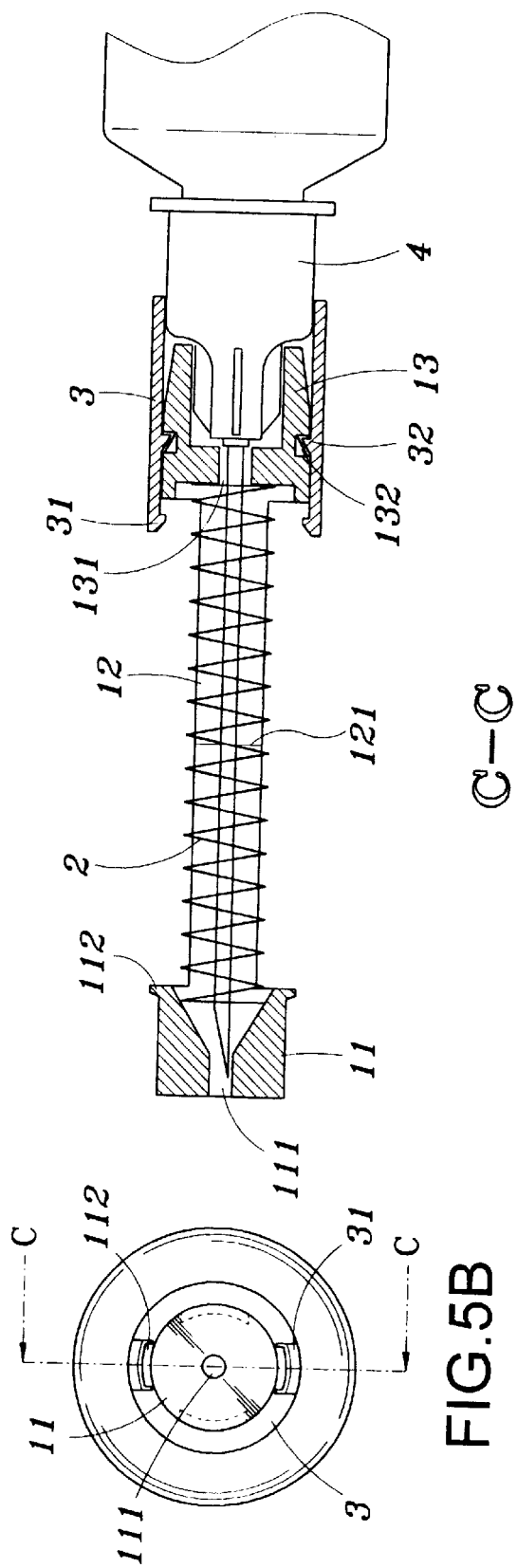
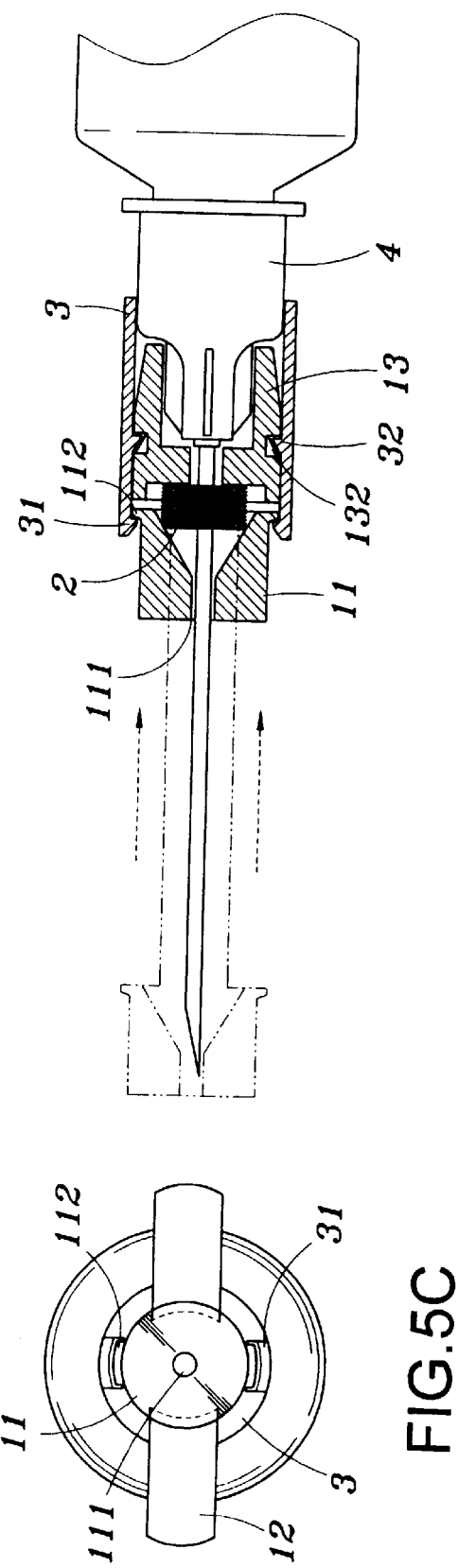
FIG.5B
FIG.5C

SYRINGE NEEDLE COVER STRUCTURE

BACKGROUND OF THE INVENTION

1. Field of the Invention

The invention herein relates to an improved structure syringe needle cover that does not involve the utilization of a removable syringe needle cover, but can be safely re-covered after injection administering, thereby preventing accidental user needlestick injury and pathogenic transmission due to blood contamination and, furthermore, ensuring the safety of both medical treatment and refuse disposal personnel as well as greater overall safe performance.

2. Description of the Prior Art

In addition to the medical treatment procedure of oral ingestion, injection is a common means of delivering medication or nutritional supplements into the human body.

The hypodermic syringe is often utilized to inject medication and, as indicated in FIG. 1, the syringe needle must be covered to prevent needlestick injuries to the user. When the syringe needle is utilized to administer an injection, the syringe needle cover is pulled off before utilization and then placed back onto the syringe needle after usage. Although the conventional injection syringe needle cover facilitates the capping of the syringe needle and, furthermore, complies with safety measures, during the removal of the syringe needle cover, since the attention of the user is usually directed to the afflicted patient, needlestick injury is likely to occur, especially when the syringe needle cover is re-capped, which then results in harmful blood contamination from transmissible diseases such as hepatitis-A, hepatitis-B and HIV, etc. Furthermore, when the conventional injection syringe needle cover is removed, the placement design of the syringe needle cover readily results in the falling off and misplacement of the syringe needle cover. Moreover, the new-type safety syringes currently being researched and developed by manufacturers are specialized structures, many of these new safety syringes being incompatible with each other and unusable with conventional syringes or so structurally complicated that the high production cost results in wasted medical treatment resources.

In view of the said shortcomings and inconveniences, the inventor of the present invention conducted extensive research to address the drawbacks based on the spirit of innovative pursuit, professional experience, and specialized knowledge to develop an improved structure syringe needle cover that complies with existing safety standards and, furthermore, is compatible with conventional injection syringe needles as well as with a wide range of new-type safety syringes to increase the applicable extent of utilization, which includes intravenous drip syringes and other hypodermic medical treatment devices, without requiring modifications to the original capping fixtures to further enhance the practical value of the invention herein.

SUMMARY OF THE INVENTION

The primary objective of the invention herein is to provide an improved structure syringe needle cover that is installed over a syringe needle and has a protective head at the upper section with a minute hole disposed through it and, furthermore, a press release section situated along the two exterior sides of the protective head, with a hollow expandable and contractible space having a number of break lines along the two sides extending through its center section; formed in the lower section is a passage that is aligned with the minute hole of the upper section and which has an annular groove disposed around the exterior and, furthermore, there is a conjoinment section at the two sides of the annular groove; a coil spring is installed into the center section of the sleeve and a mount is then attached to the lower section of the said sleeve, with latch tabs extending from its two sides engaged to the center section of the sleeve and, furthermore, there is a catch section at the lower end of the latch tabs that engages the conjoinment section at the lower section of the sleeve; when the user utilizes the syringe needle, the mount is first rotated 90 degrees counterclockwise to engage the starting end of the conjoinment section at the lower section of the sleeve to the catch section of the mount, then the press release section of the mount is pulled downward, at which time the syringe needle is extended through the minute hole disposed in the protective head of the sleeve and the latch tabs are engaged against the press release section, without requiring the removal of the syringe needle cover for utilization; when the injection is completed, the mount is rotated clockwise and after a coil spring returns to its original position in the sleeve, the catch section of the mount becomes locked onto the conjoinment section at the lower section of the sleeve such that the center section cannot be bent or broken, keeping the syringe needle from becoming exposed and thereby ensuring the safety of medical treatment personnel and achieving greater safe performance in that a syringe needle equipped with the invention herein can only be utilized once.

To enable a further understanding of the functions, structure, and innovations of the invention herein by the examination committee, the brief description of the drawing below are followed by the detailed description of the preferred embodiments.

BRIEF DESCRIPTION OF THE DRAWINGS

FIG. 5B is an orthographic drawing of an embodiment (2) of the invention herein as viewed from a frontal perspective, with a cross-sectional auxiliary drawing.

FIG. 5C is an orthographic drawing of an embodiment (3) of the invention herein as viewed from a frontal perspective, with a cross-sectional auxiliary drawing.

DETAILED DESCRIPTION OF THE PREFERRED EMBODIMENTS

Figure 2:
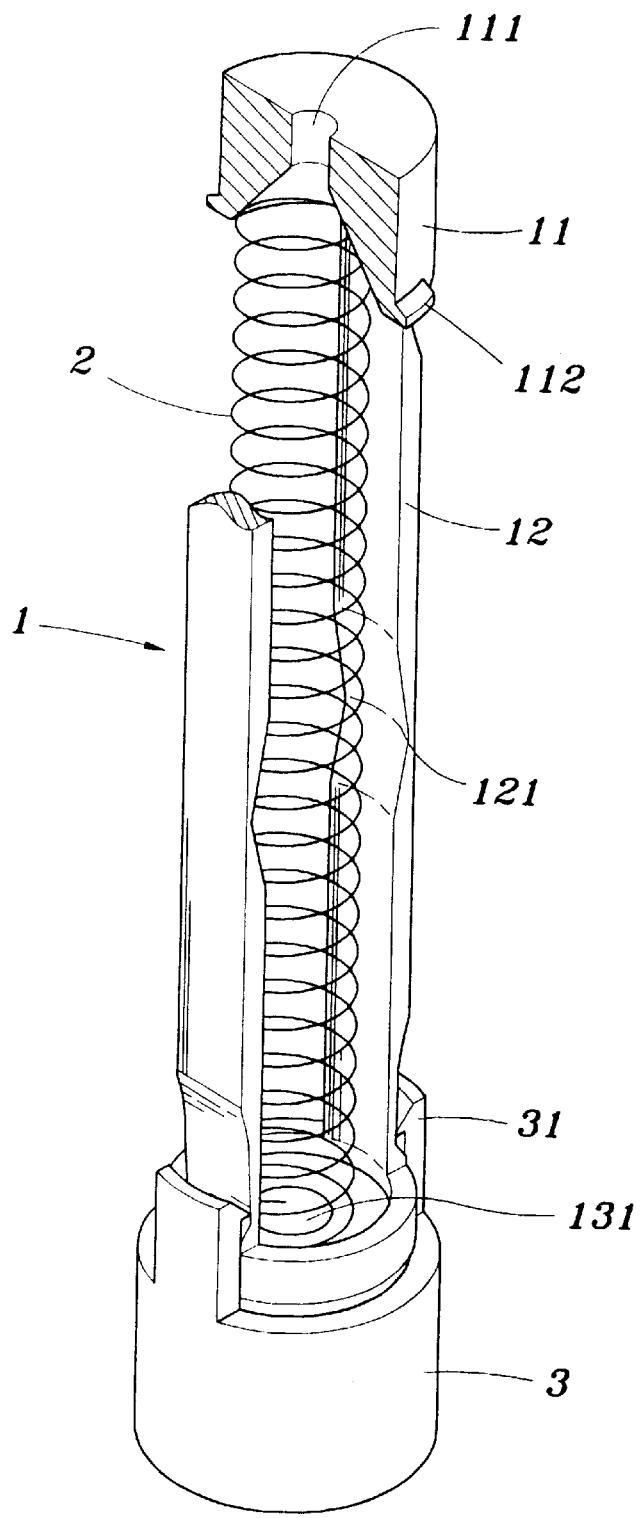
FIG. 2 is an isometric drawing of the invention herein.
Figure 3:
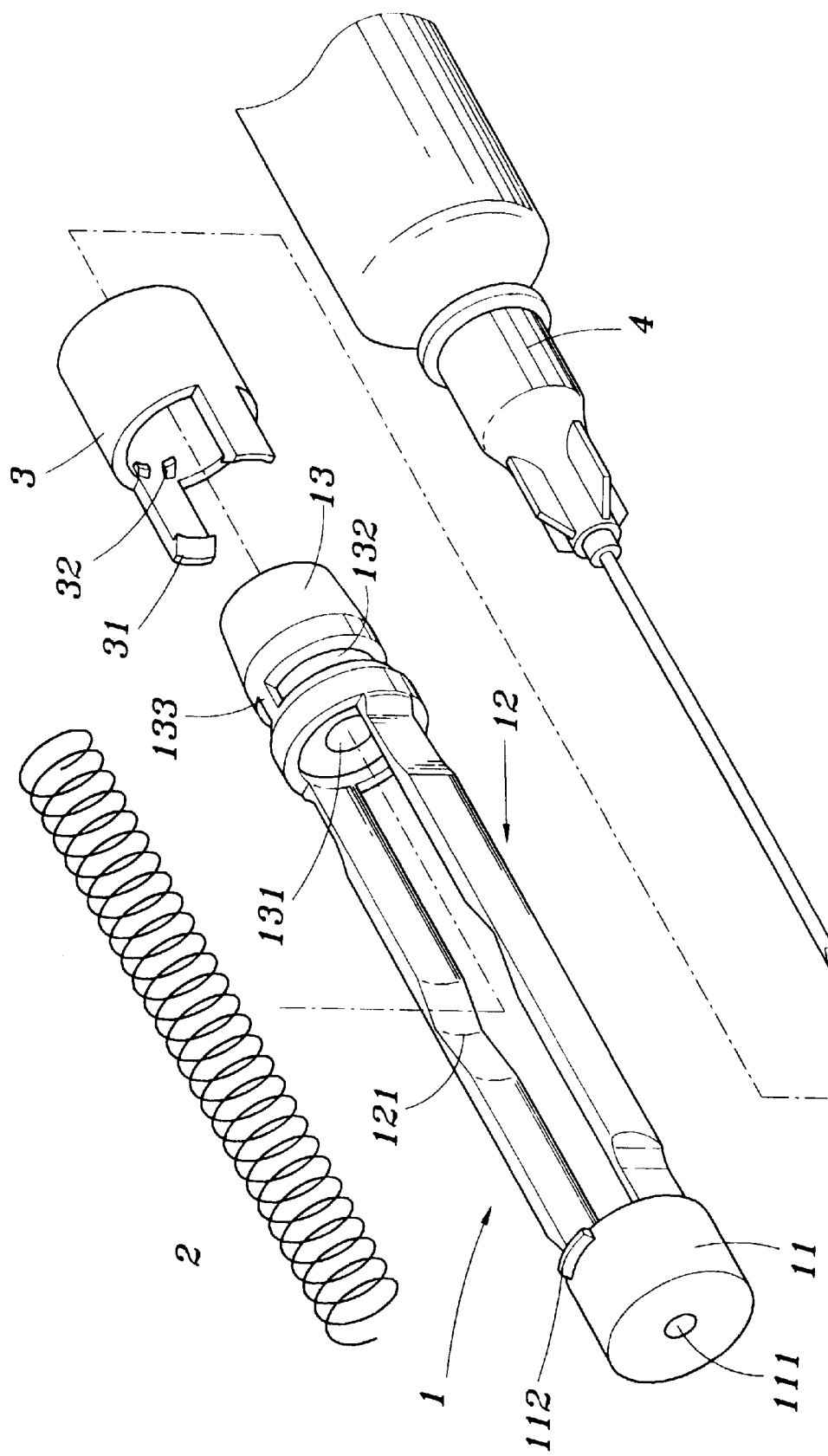
FIG. 3 is an exploded drawing of the invention herein.

Referring to FIG. 2 and FIG. 3, the invention herein is comprised of a sleeve 1, a coil spring 2, and a mount 3, wherein the sleeve 1 is installed over the syringe needle 4 and a minute hole 111 is disposed in its upper section 11, which serves as a protective head and, furthermore, a press release section 112 is situated along the two exterior sides of the protective head, a hollow expandable and contractible space having a number of break lines 121 along the two sides extends through the center section 12, and formed in the lower section 13 is a passage 131 that is aligned with the minute hole 111 of the upper section 11 and which has an annular groove 132 disposed around the exterior and, furthermore, there is a conjoinment section 133 at the two sides of the annular groove 132, with the said conjoinment section 133 having a projecting element; the coil spring 2 is installed into the center section of the sleeve 1, and the mount 2 is then attached to the lower section 13 of the said sleeve 1, with the latch tabs 31 extending from its two sides engaged to the center section 12 of the sleeve 1 and, furthermore, there is a catch section 32 at the lower end of the latch tabs 31 that engages the conjoinment section 133 at the lower section 13 of the sleeve 1; when the seams formed in the said catch section 32 of the sleeve 1 are moved after an injection is administered, the projecting element of the conjoinment section 133 at the lower section 13 of the sleeve 1 become inserted and function to secure the sleeve 1 such that sleeve does not loosen and lead to accidental injury; furthermore, the mount 3 cannot be rotated to effectively ensure single use.

Figure 4:
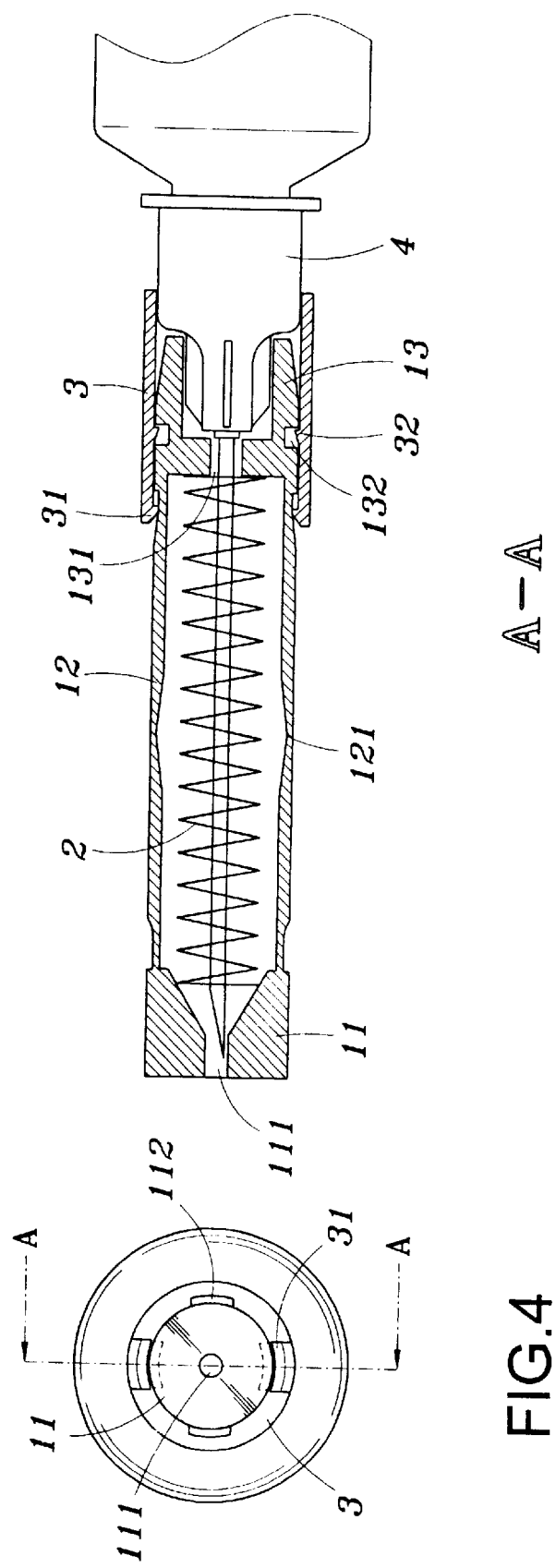
FIG. 4 is an orthographic drawing of the invention herein before use as viewed from a frontal perspective, with a cross-sectional auxiliary drawing.

Referring to FIG. 4, invention herein before utilization, the syringe needle 4 is ensheathed in the mount 3 of the invention herein, with the syringe needle 4 situated through the aligned passage 131 in the lower section 13 of the sleeve 1, the coil spring 2 within the center section 12, and the minute hole 111 in the upper section 11; the minute hole 111 through the upper section 11 of the sleeve 1 is off-center to facilitate the emergence of the syringe needle 3 when downward force is applied; the latch tabs 31 extending from the two sides of the mount 3 are engaged to the lower extent of the center section 12 of the sleeve 1 to provide a secure mechanical implementation so loosening does not occur, while the catch section 32 of the mount 3 is not yet engaged to the conjoinment section 133 of the sleeve 1.

Figure 1:
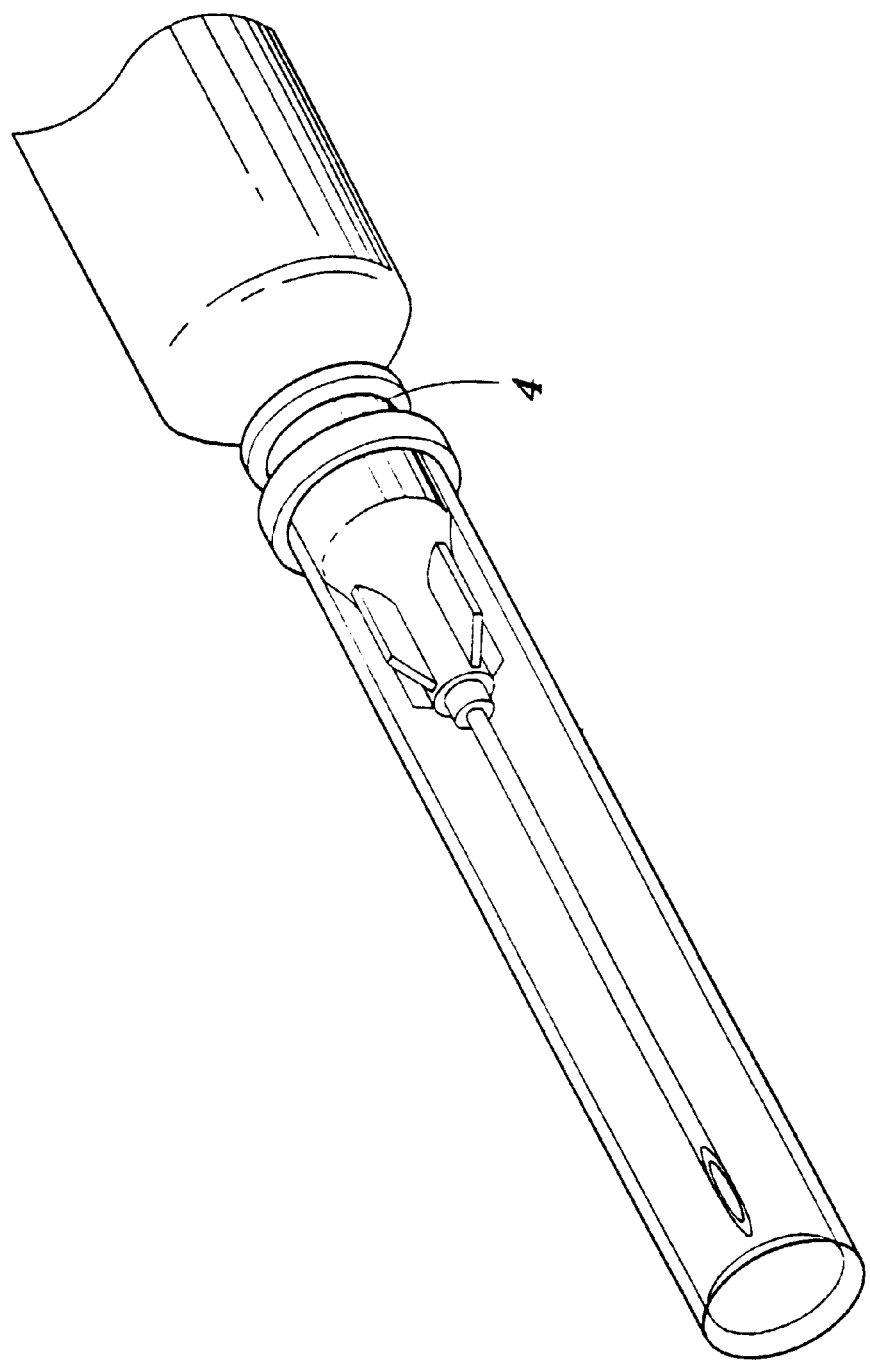
FIG. 1 an isometric drawing of a conventional syringe needle cover.
Figure 5A:
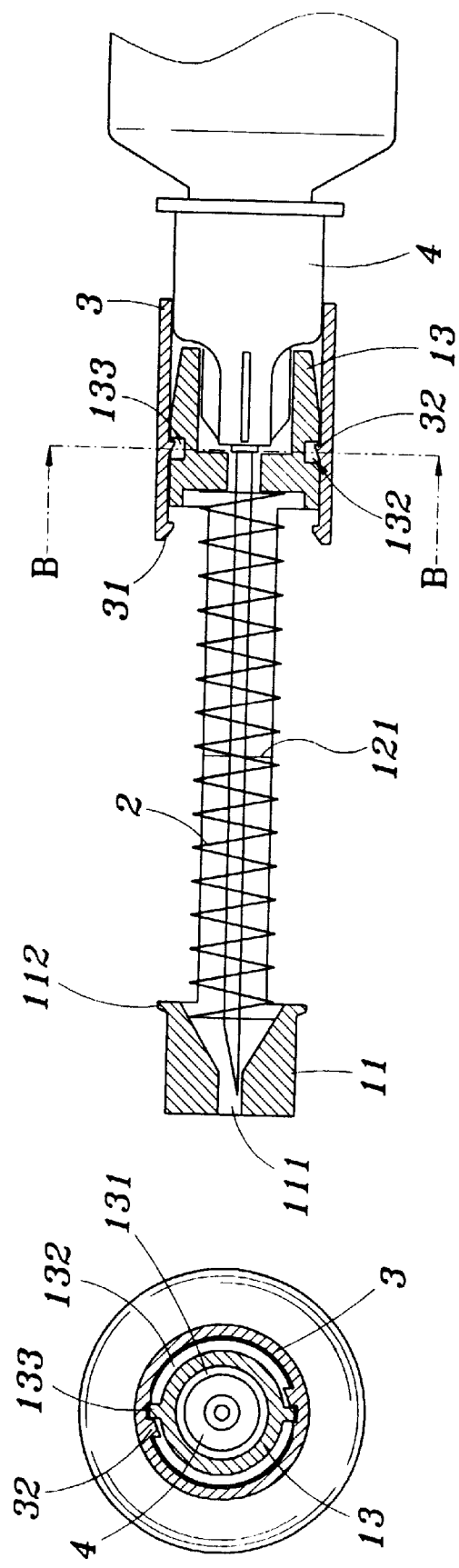
FIG. 5A is an orthographic drawing of an embodiment (1) of the invention herein as viewed from a frontal perspective, with a cross-sectional auxiliary drawing.
Figure 6:
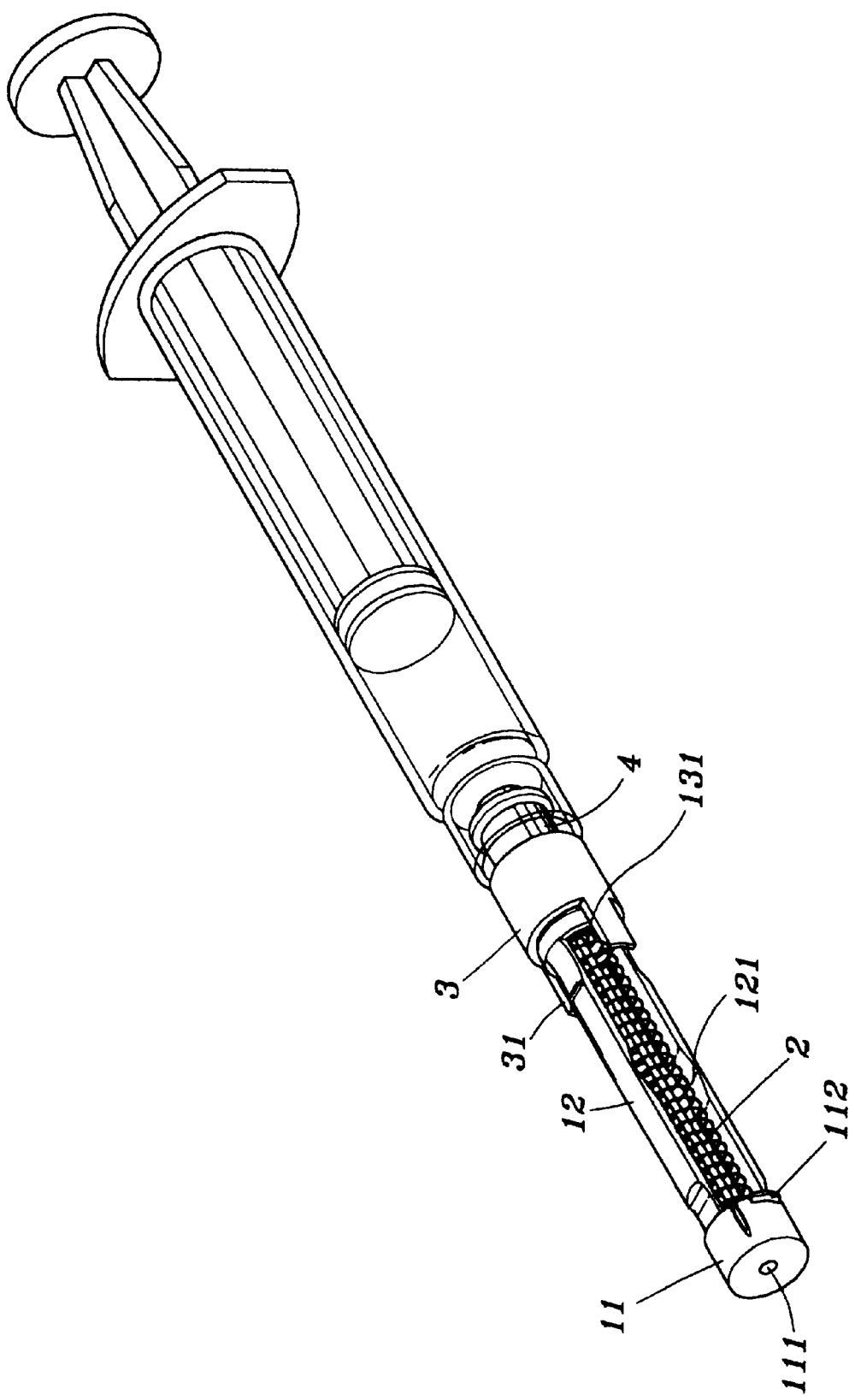
FIG. 6 is an isometric drawing of the preferred embodiment of the invention herein.

Referring to FIG. 5A, FIG. 5B, and FIG. 5C, when the invention herein is utilized, the mount 3 is rotated 90 degrees counter-clockwise to engage the conjoinment section 133 of the sleeve 1 to the catch section 32 of the mount 3, at which time the press release section 112 of the sleeve 1 becomes aligned with the latch tabs 31 of the mount 3 and then the press release section 112 is squeezed and pulled downward, upon which the center section 12 of the sleeve 1 extends outward and compresses at the break lines 121 along the two sides of the center section 12 of the sleeve 1, causing the press release section 112 to be depressed below the latch tabs 31 of the mount 3 and then the latch tabs 31 engage the press release section 112 so that the sleeve 1 is prevented from returning and syringe needle 4 is extended; when utilization is completed, the mount 3 is rotated clockwise to cause the release of the press release section 112 from the latch tabs 31 and thereby allowing the coil spring 2 to return back to its original position in the sleeve 1, at which time the mount 3 becomes locked onto the center section 12 of the sleeve 1, as indicated in FIG. 1, keeping the syringe needle 4 from becoming exposed and ensuring the safety of medical treatment and refuse disposal personnel.

In summation of the foregoing sections, since the improved structure syringe needle cover of the invention herein does not involve the utilization of a removable syringe needle cover and is automatically re-covered after the administering of an injection to prevent accidental needle puncture injury and blood contamination, the present invention achieve greater overall performance and practical value than conventional syringe needle covers or newer safety syringes and, furthermore, the said structure and its functional innovations are original and capable of increased performance, the present invention is lawfully submitted as a new patent application to the patent bureau for review and the granting of the commensurate patent rights.

However, the disclosed detailed description of the preferred embodiments and brief description of the drawings above only serve to demonstrate a workable embodiment of the invention herein and shall not be construed as a limitation of the actual scope of the invention herein, with all adaptations or modifications of the structural innovation and functions based on the said descriptions or the following claims remaining within the scope of the claims applied for by the present invention.

What is claimed is:

1. An improved structure syringe needle cover comprised of:

a sleeve that is installed over a syringe needle and has a minute hole disposed in its upper section, which serves as a protective head and, furthermore, a press release section is situated along the two exterior sides of the protective head, a hollow expandable and contractible space having a number of break lines along the two sides extends through the center section, and formed in the lower section is a passage that is aligned with the said minute hole of the said upper section and which has an annular groove disposed around the exterior and, furthermore, there is a conjoinment section at the two sides of the said annular groove;

a coil spring installed into the said center section of the said sleeve;

a mount that is attached to the said lower section of the said sleeve, with the latch tabs extending from its two sides engaged to the said center section of the said sleeve and, furthermore, there is a catch section at the lower end of the said latch tabs that engages the said conjoinment section at the said lower section of the said sleeve;

the said structure is installed over the said syringe needle such that the user is not required to handle a removable syringe needle cover and the said syringe needle automatically re-covered safely after an injection is administered and, furthermore, is rotated into a physically locked position to prevent accidental needle puncture injury to the user and subsequent blood contamination to effectively achieve increased safety.

* * * * *